United States Patent
Kizhakkedathu et al.

(10) Patent No.: US 11,357,226 B2
(45) Date of Patent: Jun. 14, 2022

(54) POLYMER BASED TRANSPLANT PRESERVATION SOLUTION

(71) Applicants: Jayachandran Kizhakkedathu, New Westminster (CA); Caigan Du, Richmond (CA); Donald Brooks, Vancouver (CA); Christopher Nguan, Vancouver (CA)

(72) Inventors: Jayachandran Kizhakkedathu, New Westminster (CA); Caigan Du, Richmond (CA); Donald Brooks, Vancouver (CA); Christopher Nguan, Vancouver (CA)

(73) Assignees: Jayachandrar Kizhakkedathu, New Westminster (CA); Caigan Du, Richmond (CA); Donald Brooks, Vancouver (CA); Christopher Nguan, Vancouver (CA)

( * ) Notice: Subject to any disclaimer, the term of this patent is extended or adjusted under 35 U.S.C. 154(b) by 0 days.

(21) Appl. No.: 16/737,371

(22) Filed: Jan. 8, 2020

(65) Prior Publication Data
US 2020/0138013 A1     May 7, 2020

Related U.S. Application Data

(62) Division of application No. 15/038,304, filed as application No. PCT/CA2014/000843 on Nov. 21, 2014, now abandoned.

(60) Provisional application No. 61/907,291, filed on Nov. 21, 2013.

(51) Int. Cl.
*A01N 1/02* (2006.01)
*A61K 35/12* (2015.01)

(52) U.S. Cl.
CPC ........... *A01N 1/0226* (2013.01); *A01N 1/021* (2013.01); *A61K 35/12* (2013.01)

(58) Field of Classification Search
CPC ....... A01N 1/0026; A01N 1/021; A61K 35/12
See application file for complete search history.

(56) References Cited

U.S. PATENT DOCUMENTS

| | | |
|---|---|---|
| 3,461,210 A | 8/1969 | Fossel |
| 4,880,629 A | 11/1989 | Okamoto et al. |
| 6,949,335 B2 | 9/2005 | Fahy et al. |
| 9,919,004 B2 | 3/2018 | Kizhakkedathu et al. |
| 2003/0202958 A1 | 10/2003 | Strickland |
| 2006/0024657 A1* | 2/2006 | Fahy .......... C09K 3/18 435/1.3 |
| 2007/0178435 A1 | 8/2007 | Fischer et al. |
| 2008/0292579 A1 | 11/2008 | Brooks et al. |
| 2010/0324150 A1 | 12/2010 | Allard et al. |
| 2015/0141512 A1 | 5/2015 | Kizhakkedathu |
| 2016/0295856 A1 | 10/2016 | Kizhakkedathu et al. |

FOREIGN PATENT DOCUMENTS

| | | | |
|---|---|---|---|
| CA | 2382864 | 4/2001 | |
| CA | 2742345 | 5/2009 | |
| EP | 1891143 | 2/2008 | |
| WO | WO03065801 | 8/2003 | |
| WO | WO-2006130978 A1 * | 12/2006 | .............. C08L 71/00 |
| WO | WO2008015015 | 2/2008 | |
| WO | WO2008074154 | 6/2008 | |
| WO | WO2009055935 | 5/2009 | |
| WO | WO-2009055935 A1 * | 5/2009 | ........... A61K 31/765 |
| WO | WO2011106877 | 9/2011 | |
| WO | WO2012162789 | 12/2012 | |
| WO | WO2013159188 | 10/2013 | |
| WO | WO2006130978 | 12/2016 | |
| WO | WO2019091290 | 5/2019 | |

OTHER PUBLICATIONS

B.O. Howden, et al, Liver Preservation with UW Solution I. Evidence That Hydroxyethyl Starch is Not Essential, 49 Transplantation 869 (Year: 1990).*
I.B. Mosbah, et al, Effects of Polyethylene Glycol and Hydroxyethyl Starch in University of Wisconsin Preservation Solution on Human Red Blood Cell Aggregation and Viscosity, 38 Transpl. Proceed. 1229 (Year: 2009).*
Andrew James McLaren & Peter John Friend, Trends in Organ Preservation, 16 Transpl. Int'l. 701 (Year: 2003).*
Mark-Hugo Maathuis, Henri Leuvenkirk & Rutger Ploeg, Perspectives in Organ Preservation, 83 Transplant. 1289 (Year: 2007).*
Class Monograph Haemodialysis Solutions, Health Canada, Oct. 9, 1996, 1-5.
European Best Practice Guideline working group on Peritoneal Dialysis, Peritoneal dialysis solutions, Nephrol Dial Transplant, 2005, 20 [Suppl 9], pp. ix16-ix20.
European Pharmacopoeia 7.0, pp. 2695-2697 (2010, implemented Jan. 2011).
European Search Opinion for Application No. EP13780839, dated Sep. 25, 2015.
European Search Report and Opinion for Application No. 14863795. 2, dated Mar. 31, 2017.
European Search Report for Application No. EP13780839, dated Sep. 25, 2015.
International Search Report for Application No. PCT/CA2013/000382 dated Aug. 1, 2013.
International Search Report for Application No. PCT/CA2014/000843 dated Feb. 27, 2015.
Agarwal, A., et al., Transplantation, "Comparison of histidine-tryptophan ketoglutarate solution and University of Wisconsin solution in prolonged cold preservation of kidney allografts", vol. 81, pp. 480-482 (2006).
Beaudette, P., et al., Anal Chem, "Development of soluble ester-linked aldehyde polymers for proteomics", vol. 83, pp. 6500-6510, (2011).

(Continued)

*Primary Examiner* — Sean M Basquill
(74) *Attorney, Agent, or Firm* — DeWitt LLP

(57) ABSTRACT

Provided are transplant preservation solutions comprising a polyglycerol wherein the polyglycerol is of a molecular weight between about 0.15 kDa and about 3.99 kDa, methods and uses thereof as well as kits providing said transplant preservation solutions.

22 Claims, 8 Drawing Sheets

(56) References Cited

OTHER PUBLICATIONS

Bleyer, A.J., et al., J. Am. Soc. Nephrol. 10(1): 154-159 (1999).
Calderon, M., et al., Adv Mater, "Dendritic polyglycerols for biomedical applications", vol. 22, pp. 190-218, (2010).
Cittanova, M.L., et al., Lancet, "Effect of hydroxyethylstarch in brain-dead kidney donors on renal function in kidney-transplant recipients", vol. 348, pp. 1620-1622, (1996).
Crawford-Bonadio & Diaz-Buxo, Nephrology Nursing Journal, "Comparison of Peritoneal Dialysis Solutions", vol. 31(5), pp. 500-509 and 520 (2004).
Davies, et al., Nephrol Dial Transplant, "The effects of low-sodium peritoneal dialysis fluids on blood pressure, thirst and volume status", vol. 24(5), pp. 1609-1617 (2009).
De Graaff, et al., Pentoneal Dialysis international, "The Effects Of A Dialysis Solution With A Combination Of Glycerol/Amino Acids/Dextrose On The Peritoneal Membrane In Chronic Renal Failure", vol. 30(2), pp. 192-200 (2010).
Dernedde, J., et al., Proc Natl Acad Set U S A, "Dendritic polyglycerol sulfates as multivalent inhibitors of inflammation", vol. 107, pp. 19679-19684. (2010).
Domenici, A., et al., Int. J Nephrol. 2011: 204216, 5 pages (2011).
Du, et al., Biomaterials, "The size-dependent efficacy and biocompatibility of hyperbranched polyglycerol in peritoneal dialysis", vol. 35, pp. 1378-1389 (2014).
Du, et al., J Transl Med, "Hyperbranched polyglycerol is superior to glucose for long-term preservation of peritoneal membrane in a rat model of chronic peritoneal dialysis", vol. 14:338, pp. 1-17 (2016).
Fang, et al., Peritoneal Dialysis International, "Comparison Between Bicarbonate/Lactate And Standard Lactate Dialysis Solution In Peritoneal Transport And Ultrafiltration: A Prospective, Crossover Single-Dwell Study", vol. 28(1), pp. 35-43 (2008).
Feriani, et al., "Solutions for peritoneal dialysis," Replacement of Renal Function by Dialysis, 505-537,Springer-Science+Business Media, B.V. (2004).
Feriani, et al., "Solutions For Peritoneal Dialysis," Replacement Of Renal Function By Dialysis, 520-545 Kluwer Academic Publishers, Dordrecht, The Netherlands (1996).
Gao, S., et al., PLoS ONE 10(2):e00116595. doi:10.1371/journal. pone.0116595, "Hyperbranched Polyglycerol as a Colloid in Cold Organ Preservation Solutions" (2015).
Garcia-Lopez, et al., Nature Reviews Nephrology, "An update on peritoneal dialysis solutions", vol. 8, pp. 224-233 (2012).
Garlicki, M., Ann Transplant, "May preservation solution affect the incidence of graft vasculopathy in transplanted heart?", vol. 8, pp. 19-24, (2003).
Gervais, M., et al., Macromolecules. "Synthesis of Linear High Molar Mass Glycidol-Based Polymers by Monomer-Activated Anionic Polymerization", vol. 43, pp. 1778-1784, (2010).
Goldfarb-Rumyantzev. A.S., et al., Am. J. Kidney Dis. 46(3): 537-549 (2005).
Grassmann, A., et al., Nephrol. Dial. Transplant 20(12): 2587-2593 (2005).
Guan, Q., et al., Surgery, "Decrease In donor heart injury by recombinant clusterin protein in cold preservation with University of Wisconsin solution", vol. 151, pp. 364-371, (2012).
Hartog, C., et al., Intensive Care Med, "CONTRA: Hydroxyethyl starch solutions are unsafe in critically ill patients", vol. 35, pp. 1337-1342, (2009).
Heaton, et al., Clinical Science. "Evaluation of glycerol as an osmotic agent for continuous ambulatory peritoneal dialysis in nd-stage renal failure", vol. 70(1), pp. 23-29 (1986).
Heimburger & Blake, Handbook of Dialysis, "Apparatus for Peritoneal Dialysis", pp. 339-355,Lippincott Nilllams & Wilkins, Philadelphia USA (2007).
Hilmi, I., et al., LiverTranspl, "The impact of postreperfusion syndrome on short-term patient and liver allograft outcome in patients undergoing orthotopic liver transplantation", vol. 14, pp. 504-508, (2008).

Hoenich & Ronco, Blood Purification, "Haemodialysis Fluid: Composition and Clinical Importance",vol. 25(1), pp. 52-68 (2007).
Kainthan R K, et al., "Biocompatibility testing of branched and linear polyglycidol",Biomacromolecules, vol. 7, No. 3, Mar. 1, 2006 (Mar. 1, 2006), pp. 703-709, XP008113075,ISSN: 1525-7797, DOI: 10.1021/BM0504882.
Kainthan, R.K., et al., Biomaterials 28(31): 4581-4590 (2007).
Kainthan, R.K., et al., Biomaterials, "Blood compatibility of novel water soluble hyperbranched polyglycerol-based multivalent cationic polymers and their interaction with DNA", vol. 27, pp. 5377-5390, (2006a).
Kainthan, R.K., et al., Biomaterials, "Hydropbobically derivatized hyperbranched polyglycerol as a human serum albumin substitute", vol. 29, pp. 1693-1704, (2008).
Kizhakkedathu, J.N., et al., Biomacromolecules, "High molecular weight polyglycerol-based multivalent mannose conjugates" vol. 11, pp. 2567-2575, (2010).
Kuznetsov, A.V., et al., Am J Physiol Heart Circ Physiol, "Mitochondrial defects and heterogeneous cytochrome c release after cardiac cold ischemia and reperfusion", vol. 285, pp. H1633-H1641, (2004).
Lang, S.M., et al., Perit. Dial. Int. 21(1): 52-58 (2001).
Lauzurica, R., et al., J Nephrol, "Pretransplant inflammation: a risk factor for delayed graft function?", vol. 21, pp. 221-228, (2008).
Li, S., et al., Am J Transl Res, "Cold preservation with hyperbranched polyglycerol-based solution improves kidney functional recovery with less injury at reperfusion in rats" vol. 9(2), pp. 429-441 (2017).
Li, S., et al., J Heart Lung Transplant, "Reduction of cold ischemia-reperfusion injury by graft-expressing cluster in in heart transplantation", vol. 30 pp. 819-826, (2011).
Li, S., et al., Journal of Surgical Research, "Advantages of replacing hydroxyethyl starch in University of Wisconsin solution with hyperbranched polyglycerol for cold kidney perfusion", vol. 205, pp. 59-69 (2016).
Lila, et al., International Journal of Pharmaceutics, "Use of polyglycerol (PG), instead of polyethylene glycol (PEG), prevents induction of the accelerated blood clearance phenomenon against long-circulating liposomes upon repeated administration", vol. 456, pp. 235-242 (2013).
Liu, Z., et al., Biomaterials, "Adsorption of amphiphilic hyperbranched polyglycerol derivatives onto human red blood cells", vol. 31, pp. 3364-3373, (2010).
Marron, B., et al., Kidney Int. Suppl. 108: S42-S51 (2008).
Mcintyre, Kidney International, "Update on peritoneal dialysis solutions", vol. 71, pp. 486-490 (2007).
Mendelson, A.A., et al., Perit Dial Int, "Hyperbranched polyglycerol is an efficacious and biocompatible novel osmotic agent in a rodent model of peritoneal dialysis", vol. 33, pp. 15-27, (2013).
Montalti, R., et al., Transplant Proc "Kidney transplantation from elderly donors: a prospective randomized study comparing celsior and UW solutions", vol. 37, pp. 2454-2455 (2005).
Mortier, et al., Kidney International, "Benefits of switching from a conventional to a low-GDP bicarbonate/lactate-buffered dialysis solution in a rat model", vol. 67, pp. 1559-1565 (2005).
Nagelschmidt, et al., The American Journal of Surgery, "Polyethylene Glycol 4000 Attenuates Adhesion Formation in Rats by Suppression of Peritoneal Inflammation and Collagen Incorporation", 176, pp. 76-80 (1998).
Nayak, K.S., et al., Contrib. Nephrol. 163: 270-277 (2009).
Pajek, et al., Nephrol Dial Tranplant, "Short-term effects of bicarbonate/ lactate-buffered and conventional lactate-buffered dialysis solutions on peritoneal ultrafiltration: a comparative crossover study", vol. 24(5), pp. 1617-1625 (2009).
Palmer, Current Medicine, "Dialysate Composition in Hemodialysis and Peritoneal Dialysis, Atlas of Diseases of the Kidney, Philadelphia," 2.1-2.8 (1999).
Perner, A., et al., N Engl J Med, "Hydroxyethyl starch 130/0.42 versus Ringer's acetate in sever sepsis", vol. 367, pp. 124-134, (2012).
Perner, A., et al., Trials, "Comparing the effect of hydroxyethyl starch 130/0.4 with balanced crystalloid solution on mortality and kidney failure in patients with severe sepsis (6S—Scandinavian

(56) References Cited

OTHER PUBLICATIONS

Starch for Severe Sepsis/Septic Shock trial): study protocol, design and rationale for a double-blinded, randomized clinical trial", vol. 12, p. 24, (2011).
Petitclerc & Jacobs, Nephrol Dial Transplant, "Dialysis sodium concentration: what is optimal and can it be individualized?", vol. 10(5) pp. 596-599 (1995).
Decaglycerol. National Centre for Biotechnology Information, PubChem Compound Database;CID=111835, https://pubchem.ncbi.nlm.nih.gov/compound/11835 (accessed Sep. 29, 2017). (Year: 2017).
Rippe, Peritoneal Dialysis International, "Hyperbranched Polyglycerol: A Future Alternative to Polyglucose in Peritoneal Dialysis Fluids?", vol. 33, No. 1, pp. 5-7 (2013).
Rippe & Venturoli, Peritoneal Dialysis International, "Optimum Electroylte Composition Of A Dialysis Solution", vol. 28 (3), pp. S131-S136 (2008).
Rossi, N.A., et al., Biomaterials, "Red blood cell membrane grafting of multi-functional hyperbranched polyglycerols", vol. 31, pp. 4167-4178, (2010).
Rubin, H.R., et al., J. Am. Med. Assoc. 291 (6):697-703 (2004).
Sault, C.M.A Journal, "Peritoneal dialysis solutions", vol. 108, pp. 325-327 (1973).
Schambye, et al., Peritoneal Dialysis International, "Bicarbonate versus Lactate-Based CAPO fluids: a Biocompatibility Study in Rabbits", vol. 12(3), pp. 281-286 (1992).
Schortgen, F., et al., Lancet "Effects of hydroxyethylstarch and gelatin on renal function in severe sepsis: a multicentre randomised study", vol. 357, pp. 911-916, (2001).
Sezer, S., et al., Transplant Proc. 43(2): 485-487 (2011).
Sharif, A., Baboolal, K., Perit. Dial. Int., vol. 31, Suppl. 2: S58-S62 (2011).
Stevens, R.B., et al., Am J Transplant, "Increased primary non-function in transplanted deceased-donor kidneys flushed with histidine-tryptophan-ketoglutarate solution", vol. 9, pp. 1055-1062,(2009).
Stiriba, S.E, et al., J Am Chem Soc, "Hyperbranched molecular nanocapsules: Comparison of the hyperbranched architecture with the perfect linear analogue", vol. 124, pp. 9698-9699, (2002).
Strijijk & Krediet, Pentoneal Dialysis International, "Sodium Balance In Automated Peritoneal Dialysis", vol. 20(2), pp. S101-S105 (2000).
Sunder, A., et al., Macromolecules, "Controlled synthesis of hyperbranched polyglycerols by ring-opening multibranching polymerization", vol. 32, pp. 4240-4246, (1999).
Theofilou, P., J Clin. Med. Res, 3(3): 132-138 (2011).
Tidball, J., Medicine and Science in Sports and Exercise, "Inflammatory cell response to acute muscle injury", vol. 27(7), pp. 1032-1032 (1995).
Trespalacos, F.C., et al., Am. J Kidney Dis. 41 (6): 1267-1277 (2003).
Turk, H., et al., Bioconjug Chem, "Dendritic polyglycerol sulfates as new heparin analogues and potent inhibitors of the complement system", vol. 15, pp. 162-167, (2004).
Ul-Haq et al., Macromol. Biosci., "Hybrid Polyglycerols with Long Blood Circulation: Synthesis, Biocompatibility, and Biodistribution", vol. 14, pp. 1469-1482 (2014).
Ul-Haq, M.I., et al., Biomaterials, "Influence of architecture of high molecular weight linear and branched polyglycerols on their biocompatibility and biodistribution". vol. 33, pp. 9135-9147, (2012).
Vonesh, E.F., et al., Kidney Int. Suppl. 103: S3-S11 (2006).
Wilms, D., et al., Acc Chem Res, "Hyperbranched polyglycerols: from the controlled synthesis of biocompatible polyether polyols to multipurpose applications", vol. 43, pp. 129-141, (2010).
Winkelmayer, et al., Kidney Int, "Hydroxyethyl starch and change in renal function in patients undergoing coronary artery bypass graft surgery", vol. 64. pp. 1046-1049, (2003).
Yang Q., et al., Clin, Nephrol. 72(1): 62-68 (2009).
James Southard and Folkert Belzer., Organ Preservation. 46 Annu. Rev. Med. 235 (Year:1995).
Application and File History for U.S. Appl. No. 15/038,304, filed May 20, 2016, inventors Kizhakkedathu et al.

\* cited by examiner

Cultured H9C2 cells

POLYMER BASED TRANSPLANT PRESERVATION SOLUTION

RELATED APPLICATIONS

This present application is a divisional of U.S. application Ser. No. 15/038,304, filed May 20, 2016, which is a U.S. National Phase entry of PCT Application No. PCT/CA2014/00843, filed Nov. 21, 2014, which claims priority to U.S. Provisional Application No. 61/907,291, filed Nov. 21, 2013, the contents of each being incorporated herein by reference in their entireties.

TECHNICAL FIELD

This invention relates to the polyglycerol field. In particular, the invention relates to transplant preservation solutions based on polyglycerols and their uses.

BACKGROUND

Flushing and storage of donor organs with a cold preservation solution is a common method to minimize the ischemic injury during donor organ procurement. Various storage solutions and technologies have been developed for this purpose with varying degrees of success, including contemporary perfusate technology. Delayed graft function (DGF) is a problem that may be found in renal allografts from extended criteria donors that are flushed and stored with some of the currently used University of Wisconsin (UW), Celsior and Histidine Tryptophan Ketoglutarate (HTK) solutions (Agarwal, A., Murdock, P., Fridell, J. A., 2006. Comparison of histidine-tryptophan ketoglutarate solution and University of Wisconsin solution in prolonged cold preservation of kidney allografts. Transplantation 81, 480-482.; Montalti, R., Nardo, B., Capocasale, E., Mazzoni, M. P., Dalla Valle, R., Busi, N., Beltempo, P., Bertelli, R., Puviani, L., Pacile, V., Fuga, G., Faenza, A., 2005. Kidney transplantation from elderly donors: a prospective randomized study comparing celsior and UW solutions. Transplant Proc 37, 2454-2455; and Stevens, R. B., Skorupa, J. Y., Rigley, T. H., Yannam, G. R., Nielsen, K. J., Schriner, M. E., Skorupa, A. J., Murante, A., Holdaway, E., Wrenshall, L. E., 2009. Increased primary non-function in transplanted deceased-donor kidneys flushed with histidine-tryptophan-ketoglutarate solution. Am J Transplant 9, 1055-1062).

Different preservation solutions substantially differ in their composition, but often they aim to prevent cellular and interstitial edema, and cell death, thus, aiming to maximize organ function after transplantation. UW solution is used for both aortic in situ flush and ex vivo cold storage of the kidney, liver and pancreas. However, the inclusion of hydroxyethyl starch (HES) in UW solution can have a negative impact on its application in cold preservation of organs, particularly from deceased donors. HES is commonly used as a colloid for volume resuscitation of critically ill patients, but its safety has recently come into question; fluid resuscitation with HES is associated with coagulopathy, pruritus and acute kidney injury (Hartog, C., Reinhart, K., 2009. CONTRA: Hydroxyethyl starch solutions are unsafe in critically ill patients. Intensive Care Med 35, 1337-1342; Perner, A., Haase, N., Guttormsen, A. B., Tenhunen, J., Klemenzson, G., Aneman, A., Madsen, K. R., Moller, M. H., Elkjaer, J. M., Poulsen, L. M., Bendtsen, A., Winding, R., Steensen, M., Berezowicz, P., Soe-Jensen, P., Bestle, M., Strand, K., Wiis, J., White, J. O., Thornberg, K. J., Quist, L., Nielsen, J., Andersen, L. H., Holst, L. B., Thormar, K., Kjaeldgaard, A. L., Fabritius, M. L., Mondrup, F., Pott, F. C., Moller, T. P., Winkel, P., Wetterslev, J., 2012. Hydroxyethyl starch 130/0.42 versus Ringer's acetate in severe sepsis. N Engl J Med 367, 124-134; Perner, A., Haase, N., Wetterslev, J., Aneman, A., Tenhunen, J., Guttormsen, A. B., Klemenzson, G., Pott, F., Bodker, K. D., Badstolokken, P. M., Bendtsen, A., Soe-Jensen, P., Tousi, H., Bestle, M., Pawlowicz, M., Winding, R., Bulow, H. H., Kancir, C., Steensen, M., Nielsen, J., Fogh, B., Madsen, K. R., Larsen, N. H., Carlsson, M., Wiis, J., Petersen, J. A., Iversen, S., Schoidt, O., Leivdal, S., Berezowicz, P., Pettila, V., Ruokonen, E., Klepstad, P., Karlsson, S., Kaukonen, M., Rutanen, J., Karason, S., Kjaeldgaard, A. L., Holst, L. B., Wernerman, J., 2011. Comparing the effect of hydroxyethyl starch 130/0.4 with balanced crystalloid solution on mortality and kidney failure in patients with severe sepsis (6S—Scandinavian Starch for Severe Sepsis/Septic Shock trial): study protocol, design and rationale for a double-blinded, randomised clinical trial. Trials 12, 24; Schortgen, F., Lacherade, J. C., Bruneel, F., Cattaneo, I., Hemery, F., Lemaire, F., Brochard, L., 2001. Effects of hydroxyethyl-starch and gelatin on renal function in severe sepsis: a multicentre randomised study. Lancet 357, 911-916; and Winkelmayer, W. C., Glynn, R. J., Levin, R., Avorn, J., 2003. Hydroxyethyl starch and change in renal function in patients undergoing coronary artery bypass graft surgery. Kidney Int 64, 1046-1049), and impairs immediate donor kidney function after transplantation (Cittanova, M. L., Leblanc, I., Legendre, C., Mouquet, C., Riou, B., Coriat, P., 1996. Effect of hydroxyethylstarch in brain-dead kidney donors on renal function in kidney-transplant recipients. Lancet 348, 1620-1622).

Hyperbranched polyglycerol (HPG) is a water-soluble branched polyether polymer that has been investigated for many medical applications, such as restoring the circulation volume as an albumin substitute (Kainthan, R. K., Janzen, J., Kizhakkedathu, J. N., Devine, D. V., Brooks, D. E., 2008. Hydrophobically derivatized hyperbranched polyglycerol as a human serum albumin substitute. Biomaterials 29, 1693-1704.) and in peritoneal dialysis solution as a primary osmotic agent (Mendelson, A. A., Guan, Q., Chafeeva, I., da Roza, G. A., Kizhakkedathu, J. N., Du, C., 2013. Hyperbranched polyglycerol is an efficacious and biocompatible novel osmotic agent in a rodent model of peritoneal dialysis. Pent Dial Int 33, 15-27). HPG is a highly water soluble (>400 mg/mL) and compact polymer, has an equal or better biocompatibility profile compared to polyethylene glycol (PEG), HPG has low intrinsic viscosity that is similar to that of proteins and is approximately 10-times lower than that of linear polymers (i.e. PEG, HES, dextran) (Kainthan, R. K., Janzen, J., Kizhakkedathu, J. N., Devine, D. V., Brooks, D. E., 2008. Hydrophobically derivatized hyperbranched polyglycerol as a human serum albumin substitute. Biomaterials 29, 1693-1704; and ul-Haq, M. I., Lai, B. F. L., Chapanian, R., Kizhakkedathu, J. N., 2012. Influence of architecture of high molecular weight linear and branched polyglycerols on their biocompatibility and biodistribution. Biomaterials 33, 9135-9147); and HPG neither precipitates proteins nor aggregates the cells (e.g. RBCs) even at very high concentrations (Liu, Z., Janzen, J., Brooks, D. E., 2010. Adsorption of amphiphilic hyperbranched polyglycerol derivatives onto human red blood cells. Biomaterials 31, 3364-3373; Rossi, N. A., Constantinescu, I., Kainthan, R. K., Brooks, D. E., Scott, M. D., Kizhakkedathu, J. N., 2010. Red blood cell membrane grafting of multi-functional hyperbranched polyglycerols. Biomaterials 31, 4167-4178; and ul-Haq, M. I., Lai, B. F. L., Chapanian, R., Kizhakkedathu, J. N., 2012. Influence of architecture of high molecular weight linear and branched polyglycerols on their biocompatibility and biodistribution. Biomaterials 33, 9135-9147).

SUMMARY

In one aspect, the present invention provides a transplant preservation solution comprising a polyglycerol wherein the polyglycerol is of a molecular weight between about 0.15 kDa and about 3.99 kDa. In some embodiments, the molecular weight of the polyglycerol is between about 0.20 kDa and about 3.95 kDa, or between about 0.50 kDa and about 3 kDa, or between about 0.75 kDa to about 2.0 kDa. The molecular weight (MW) of each polymer is determined by using Gel Permeation Chromatography (GPC) and nuclear magnetic resonance (NMR) spectroscopy.

In some embodiments, the transplant preservation solution is in aqueous solution. In one embodiment, the polyglycerol comprises about 0.01% by weight to about 50% by weight of the transplant preservation solution solution, about 0.20% by weight to about 40% by weight of the transplant preservation solution solution, about 0.40% by weight to about 30% by weight of the transplant preservation solution solution, about 0.60% by weight to about 25% by weight of the transplant preservation solution solution, about 1.00% by weight to about 23% by weight of the transplant preservation solution solution, or about 1.25% by weight to about 20% by weight of the transplant preservation solution solution.

In some embodiments, the pH of the transplant preservation solution is between about 2.0 and about 9.0, between about 5.0 and about 7.9, between about 5.1 and about 7.9, between about 6.0 and about 7.6, between about 6.1 and about 7.6, between about 6.2 and about 7.6, between about 6.3 and about 7.6, between about 6.4 and about 7.6, or between about 6.5 and about 7.5.

In some embodiments, the transplant preservation solution has an osmolarity between about 150 milliosmols per litre and about 1500 milliosmols per litre, between about 240 and about 600 milliosmols per litre, between about 290 milliosmols per litre and about 580, between about 290 milliosmols per litre and about 480 milliosmols per litre, about 290 milliosmols per litre and about 460 milliosmols per litre, or between about 290 milliosmols per litre and about 450 milliosmols per litre, In some embodiments, the degree of branching of the polyglycerol is between about 0.5 and about 0.7, between about 0.6 and about 0.7, between about 0.5 and about 0.6, between about 0.55 and about 0.7, or between about 0.55 and about 0.65.

In some embodiments, the transplant preservation solution comprises at least two polyglycerols wherein the molecular weight of each of the at least two polyglycerols are different. In some embodiments, the transplant preservation solution comprises polyglycerols of a single molecular weight. In embodiments in which the transplant preservation solution comprises polyglycerols of a single molecular weight, some of those embodiments comprise a single polyglycerol and other embodiments comprise at least two polyglycerols having the same molecular weight but different chemical structures.

In some embodiments, the polyglycerol may further comprise one or more hydrophobic groups, hydrophilic groups or both. In some embodiments, the one or more hydrophobic groups, hydrophilic groups or both are joined to form from about 1% to about 100% of hydroxyl groups on the polyglycerol. In some embodiments, the one or more hydrophobic groups, hydrophilic groups or both are joined to form from about 1% to about 40% of hydroxyl groups on the polyglycerol. In some embodiments, the one or more hydrophobic groups, hydrophilic groups or both comprise one or more of a carboxylic acid, an amine, a substituted amine, an amino acid, a phosphate, a sulfate, an alkyl, an alkyl ether, an aromatic group, a zwitterionic group, a carbohydrate, metal chelating groups, reactive oxygen scavenging groups, a disulfide or a thiol.

In some embodiments, the transplant preservation solution further comprises one or more of antioxidants, nucleosides, acids, bases, xanthine oxidase inhibitor, diffusion agent, osmotic agent, lactobionic acid, vitamins, proteins, growth factors, anti-inflammatory agents, cell death inhibitors, cell membrane stabilizing agents, antibiotics.

In some embodiments, the present invention provides a transplant preservation solution comprising a hyperbranched polyglycerol (HPG) as described herein.

In some embodiments, the present invention provides a transplant preservation solution comprising a hyperbranched polyglycerol wherein the hyperbranched polyglycerol is of a molecular weight between about 0.15 kDa and about 3.99 kDa. In a further embodiment, the molecular weight of the polyglycerol is between about 0.20 kDa and about 3.95 kDa, or about 0.50 kDa and about 3 kDa, or about 1.0 kDa to about 2.0 kDa.

In another aspect, use of a transplant preservation solution as described herein for limiting donor organ injury during organ procurement and transplant, wherein organ transplants may be allografts, isografts or autografts. Wherein organs can include the heart, kidneys, liver, lungs, pancreas, intestine, spleens, limbs including fingers/toes, sex organs and thymus.

In another aspect, use of a transplant preservation solution as described herein is provided for limiting donor tissue injury during tissue procurement and transplant, wherein tissue transplants may be allografts, isografts or autografts. Such tissues may include bones, tendons (both referred to as musculoskeletal grafts), cornea, skin, heart valves, islets, part of and whole face, nerves and blood vessels.

In another aspect, use of a transplant preservation solution as described herein is provided for limiting donor cell injury during cell procurement and transplant. Such cells may include endothelial cells, pancreatic cells, stem cells and immune cells.

In another aspect, use of a transplant preservation solution is provided for limiting donor organ, tissue or cell injury ex-vivo. In some embodiments, an organ has a greater chance of maintaining organ function. In some embodiments, the organs may be kept for longer periods of time outside a body.

In some embodiments, the transplant preservation solution may be used to reduce and/or minimize the damaging effects of cold ischemia and warm reperfusion on organ, tissue or cell function during organ procurement and transplant.

In some embodiments, the transplant preservation solution may be used at a low temperature. In some embodiments the temperature of the transplant preservation solution may be between 0 and 25 degrees Celsius. In some embodiments the temperature of the transplant preservation solution may be between 0 and 10 degrees Celsius. In some embodiments, the temperature of the transplant preservation solution may be between 1 and 6 degrees Celsius. In some embodiments, the temperature of the transplant preservation solution may be between 2 and 5 degrees Celsius.

In some embodiments, the transplant preservation solution may be used at mammalian body temperature. In some embodiments, the temperature of the transplant preservation solution may be between 25 and 40 degrees Celsius. In some embodiments the temperature of the transplant preservation solution may be between 29 and 38 degrees Celsius. In some embodiments the temperature of the transplant preservation solution may be between 35 and 38 degrees Celsius.

In accordance with a further aspect of the invention, methods are provided for treating a patient having organ failure, the methods comprising procuring an organ and maintaining it in a transplant preservation solution, and transplanting said organ to the patient. In some embodiments, the organ may be from the patient. In some embodiments, the organ may be from a person different from the patient.

In accordance with a further aspect of the invention, methods are provided for treating a patient having tissue disease, tissue destruction or tissue malfunction, the methods comprising procuring tissue and maintaining it in a transplant preservation solution, and transplanting said tissue to the patient. In some embodiments, the tissue may be from the patient. In some embodiments, the tissue may be from a person different from the patient.

In accordance with a further aspect of the invention, methods are provided for treating a patient having cell based disease, cell based destruction or cell based malfunction, the methods comprising procuring cells and maintaining them in a transplant preservation solution, and transplanting said cells to the patient. In some embodiments, the tissue may be from the patient. In some embodiments, the tissue may be from a person different from the patient.

In one aspect, the present invention provides a kit for formulating a transplant preservation solution, the kit comprising a lyophilized polyglycerol wherein the polyglycerol is of a molecular weight between about 0.15 kDa and about 3.99 kDa and instructions for using the lyophilized polyglycerol for formulating the transplant preservation solution. In another embodiment, the kit further comprises one or more amino acids, diffusion agents, and/or osmotic agents.

In a further aspect, the present invention provides a composition comprising a transplant preservation solution as described herein and at least one physiologically acceptable salt, buffer, diluent and/or excipient, for use in limiting injury to a donor organ, donor tissue or donor cell. In some embodiments, the composition is in aqueous solution. In another embodiment, the composition is a lyophilized product.

In another aspect, a transplant preservation solution as described herein may be used in the transplant of an organ to a person with organ failure or with organ disease.

In another aspect, a transplant preservation solution as described herein may be used in the removal from an organ donor of a heart, kidney, liver, lung, pancreas, intestine, spleen, limbs including fingers/toes, sex organs or thymus.

In another aspect, a transplant preservation solution as described herein may be used in the removal of tissue from a tissue donor.

In another aspect, a transplant preservation solution as described herein may be used in the removal of cells from a cell donor.

In accordance with another aspect of the invention, methods are provided for keeping a transplant organ, transplant tissue, or transplant cell viable, the methods comprising contacting the organ, tissue or cell with a transplant preservation solution as described herein.

DETAILED DESCRIPTION

Figure 1:
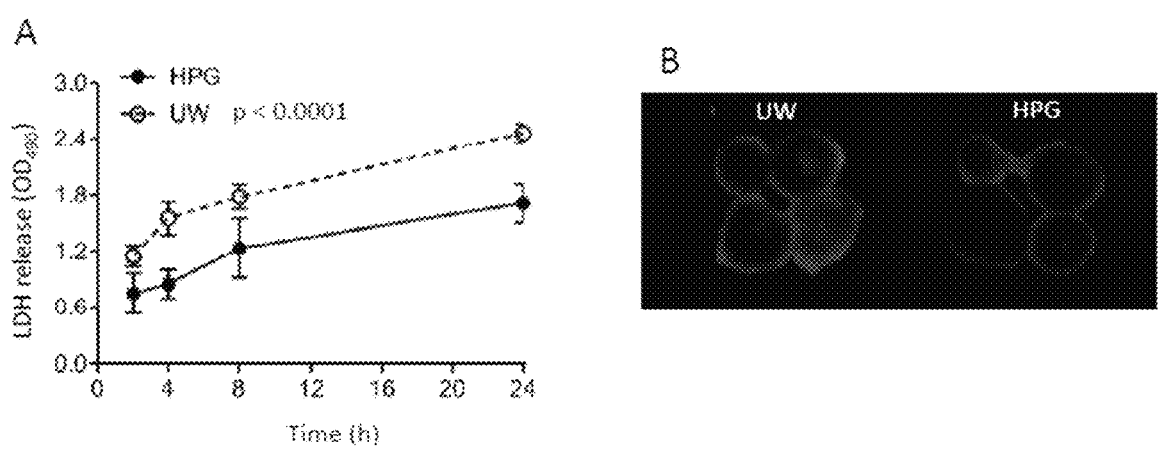
FIG. 1: Less tissue damage in mouse hearts preserved with HPG transplant preservation solution. The hearts from naïve B6 mice were stored in HPG or UW solution (0.2 mL/organ) at 4° C. for 24 h. (A) The tissue damage of the hearts was determined by LDH release to the preservation solution. Data are presented as mean±SEM. Two-way ANOVA was used for statistical analyses (p<0.0001, HPG vs. UW, n=4-7). (B) A representative image of EB-stained heart slices after 24-h cold preservation with HPG or UW solution. The hearts were stained with 0.5 µg/mL of EB in PBS for 15 min after cold preservation. After removal of unbound EB by extensive washing with PBS, the hearts were sliced transversely into four pieces. The fluorescence intensity in dead cells stained with EB was visualized with UV light.

Any terms not directly defined herein shall be understood to have the meanings commonly associated with them as understood within the art of the invention.

The term "polyglycerol" is used herein as it is normally understood to a person of ordinary skill in the art and often refers to a polymer having a degree of branching, e.g., between 0 and 1.0 wherein the number of hydroxyl groups is equal to the number of repeat units and the repeat units consist of the following (wherein "r" is the repeat unit):

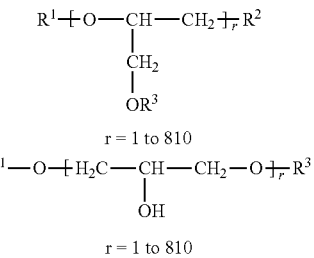

r = 1 to 810 r = 1 to 810 wherein $R^1$ is H—, $CH_3$—, $CH_3CH_2$—, t-Bu-, $N_3$—$CH_2$—$CH_2$, alkyl chains (1 to 18 carbons), —$CH_2$—$NH_2$, —$CH_2$—$N(CH_3)_2$, —$CH_2$—$NH(CH_3)$, r-, r-$CH_2$— or (r-)$_2$CH—; $R^2$ is -r, —O-r, —O—$CH_2$—CH-r, or —OH; and $R^3$ is —H, —$CH_3$, —$CH_2$—$CH_3$, r-, —$CH_2$-r or —CH(-r)$_2$. The foregoing repeat units are not limited to the stereochemistry shown. Examples of "polyglycerol" include a hyperbranched polyglycerol (HPG), a linear polyglycerol (LPG), or dendritic polyglycerol/polyglycerol dendrimer or chemically modified polyglycerol or biodegradable polyglycerol, comb-like polyglycerol or dendri-graft polyglycerol or cyclic polyglycerol or a combination thereof. The embodiments of the polyglycerol as described herein include all possible stereochemical alternatives, including those illustrated or described herein.

The term "hyperbranched polyglycerol" is used herein as it is normally understood to a person of ordinary skill in the art and often refers to a polyglycerol having a degree of branching between about 0.5 and about 0.7.

The term "linear polyglycerol" is used herein as it is normally understood by a person of ordinary skill in the art, and often refers to a polyglycerol having degree of branching "zero".

The term "dendritic polyglycerol or polyglycerol dendrimer" is used herein as it is normally understood by a person of ordinary skill in the art, and often refers to a polyglycerol having degree of branching 1.0.

The term "osmotic agent" is used herein as it is normally understood to a person of ordinary skill in the art and often refers to a substance that creates an osmotic gradient across a semi-permeable membrane to cause the movement of water across the membrane.

The term "diffusion agent" is used herein as it is normally understood to a person of ordinary skill in the art and often refers to a substance that creates a concentration gradient across a membrane to cause the movement of solutes from an area of higher solute concentration to an area of lower solute concentration.

The term "electrolyte" is used herein as it is normally understood to a person of ordinary skill in the art and often refers to an ionized solute.

As used herein, the term "alkyl" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (e.g. $C_1$-$C_{10}$ or 1- to 10-membered means one to ten carbons), or if undesignated is a $C_1$-$C_{10}$ alkyl. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "substituted" refers to the replacement of a hydrogen atom on a compound with a substituent group. A substituent may be a non-hydrogen atom or multiple atoms of which at least one is a non-hydrogen atom and one or more may or may not be hydrogen atoms. For example, without limitation, substituted compounds may comprise one or more substituents selected from the group consisting of: R", OR", NR"R'", SR", halogen, SiR"R'"R"", OC(O)R", C(O)R", CO$_2$R", CONR"R'", NR'"C(O)$_2$R", S(O)R", S(O)$_2$R", CN and NO$_2$.

As used herein, each R", R'", and R"" may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

The term "transplant preservation solution" is used herein as it is normally understood to a person of ordinary skill in the art and often refers to a substance that can be used minimize the damaging effects of cold ischemia and warm reperfusion on organs or tissue during transplant. Terms with a similar meaning include transplant solution, preservation solution, organ preservation solution, preservations solution for transplant. Some examples of typical compositions of some non-limiting examples of transplant preservation solutions known in the art are include, but are not limited to University of Wisconsin (UW) solutions and HTK solutions. HTK-type solutions are organ preservation solutions that comprise histidine, tryptophan and ketoglutarate, whereas UW-type solutions do not comprise histidine, tryptophan and ketoglutarate. Some examples of the compositions of these types of organ preservation solutions are provided below:

| Base components of a typical UW-type transplant preservation solution |
| --- |
| lactobionic acid |
| Potassium phosphate monobasic |
| Magnesium Sulfate heptahydrate |
| Raffinose pentahydrate |
| Adenosine |
| Glutathione |
| Allopurinal |
| KOH |
| Hydroxyethyl Starch |

| Base components of a typical HTK-type transplant preservation solution |
| --- |
| Sodium |
| Potassium |
| Magnesium |
| Calcium |
| Ketoglutarate/glutamic acid |
| Histidine |
| Mannitol |
| Tryptophan |

| Composition of UW solution | |
| --- | --- |
| | Viaspan ™ (DuPont) UW solution |
| Lactobionic acid | 100 mM |
| KOH | 100 mM |
| KH$_2$PO$_4$ | 25 mM |
| MgSO$_4$ | 5 mM |
| Adenosine | 5 mM |
| Glutathione | 3 mM |
| Allopurinol | 1 mM |
| Raffinose | 30 mM |
| Hydroxyethyl starch | 50 g/L |
| NaOH/HCl: pH 7.4 | + |
| Osmolarity | 320 mOsmol/kg |

| Composition of HTK solution | |
| --- | --- |
| | Custodiol ™ HTK |
| NaCl (mM) | 15 |
| KCl (mM) | 9 |
| Potassium hydrogen ketoglutarate (mM) | 1 |
| MgCl (mM) | 4 |

| Composition of HTK solution | |
| --- | --- |
| | Custodiol ™ HTK |
| Histidine* (mM) | 198 |
| CaCl (μM) | 15 |
| Tryptophan (mM) | 2 |
| Mannitol (mM) | 30 |
| Osmolality: | 310 mOsmol/kg |

The above examples of known organ preservation solutions may be used as a basis for preparing transplant preservation solutions of the present invention. In some embodiments, a transplant preservation solution of the present invention may be prepared by adding a polyglycerol as described herein to a known organ preservation solution. In some embodiments, modifications to known organ preservation solutions may be made in addition to adding a polyglycerol as described herein. Below are some non-limiting examples of transplant preservation solutions of the present invention compared to a known organ preservation solution.

| Composition and Comparison of HPG-UW solution | | |
| --- | --- | --- |
| | Viaspan ™ (DuPont) UW solution | HPG-UW solution |
| Lactobionic acid | 100 mM | 100 mM |
| KOH | 100 mM | 100 mM |
| KH$_2$PO$_4$ | 25 mM | 25 mM |
| MgSO$_4$ | 5 mM | 5 mM |
| Adenosine | 5 mM | 5 mM |
| Glutathione | 3 mM | 3 mM |
| Allopurinol | 1 mM | 1 mM |
| Raffinose | 30 mM | None |
| Hydroxyethyl starch | 50 g/L | None |
| HPG | None | 30 g/L |
| NaOH/HCl: pH 7.4 | + | + |
| Osmolarity | 320 mOsmol/kg | 320 mOsmol/kg |

| Composition and Comparison of HPG-HTK solution | | |
| --- | --- | --- |
| | Custodiol ™ HTK | HPG-HTK |
| NaCl (mM) | 15 | 15 |
| KCl (mM) | 9 | 9 |
| Potassium hydrogen ketoglutarate (mM) | 1 | 1 |
| 4 mM MgCl (mM) | 4 | 4 |
| Histidine* (mM) | 198 | 168 |
| CaCl (μM) | 15 | 15 |
| Tryptophan (mM) | 2 | 2 |
| Mannitol (mM) | 30 | None |
| HPG (g/100 mL) | None | 3 (3%, 1 kDa) |
| pH 7.02-7.2 at 25° C. | + | + |
| pH 7.4-7.45 at 4° C. | | |
| Osmolality: | 310 mOsmol/kg | 310 mOsmol/kg |

Transplant preservation solutions of the present invention do not comprise lactate. For example ringer's lactate solution has been used as an organ preservation solution, however embodiments comprising lactate are not included in the present invention.

An example of particular embodiments of the invention includes, a polyglycerol as described herein together with the components of a UW-type solution that does not comprise raffinose or hydroxyethyl starch. A particular embodiment includes a polyglycerol as described herein together with the components of Viaspan™, excepting raffinose and hydroxyethyl starch.

More generally, the transplant preservation solutions of the present invention comprise a typical lactate free organ preservation solution, including those known in the art, and further comprise a polyglycerol wherein the polyglycerol is of a molecular weight between about 0.15 kDa and about 3.99 kDa or between about 0.5 kDa and about 3.0 kDa or between about 0.75 kDa and about 2.0 kDa. Polyglycerol is a flexible, hydrophilic aliphatic polyether polymer which can be synthesized in linear, hyperbranched and dendrimeric forms with precise control of molecular weight. The circulation half-life in mice often depends on the molecular weight of the polymer, but may reach about 60 hours for a molecular weight of 540 kDa. Polyglycerols for use in the present invention may contain glucose or carbohydrate and are stable and easily delivered at physiological pH.

Hyperbranched polyglycerol (HPG), which is a polyglycerol having a degree of branching between about 0.5 and about 0.7, is prepared by multi-branching ring opening polymerization of glycidol under slow monomer addition. Polyglycerol dendrimers are prepared by multiple organic reactions. The structure contains large and small branches with hydroxyl-functionalities that render HPG a highly functional material. Linear polyglycerol (LPG) may be prepared by ring opening polymerization of ethoxy ethyl glycidyl ether using t-BuO$^-$K$^+$ as initiator in the presence of 1,4-dioxane followed by deprotection in HCl (Gervais, M., Brocas, A. L., Cendejas, G., Deffieux, A., Carlotti, S., 2010. Synthesis of Linear High Molar Mass Glycidol-Based Polymers by Monomer-Activated Anionic Polymerization. Macromolecules 43, 1778-1784; Kainthan, R. K., Janzen, J., Levin, E., Devine, D. V., Brooks, D. E., 2006b. Biocompatibility testing of branched and linear polyglycidol. Biomacromolecules 7, 703-709; and Stiriba, S. E., Kautz, H., Frey, H., 2002. Hyperbranched molecular nanocapsules: Comparison of the hyperbranched architecture with the perfect linear analogue. J Am Chem Soc 124, 9698-9699).

Polyglycerol is a clear, viscous liquid. At room temperature, it is highly viscous and essentially non-volatile. Both linear and hyperbranched polyglycerols are of a compact nature in solution and highly soluble in water (for example, HPG has a water solubility greater than 200 mg/mL). The hydrodynamic radius ($R_h$) of a LPG with $M_n$=104,000 in aqueous 0.1 N NaNO$_3$ solution may be 4.55 nm as determined by QELS measurements. For comparison, the $R_h$ value of an HPG with $M_n$=104,000 may be 4.85 nm and a PEG with similar molecular weight may be 12.23 nm. The very small $R_h$ value of LPG indicates that it has quite a different solution structure compared to other linear water soluble polymers and may more closely approximate the solution structure and properties of HPG. In terms of intrinsic viscosity, LPG has an intrinsic viscosity (0.047 dL/g) that is more similar to that of HPG (0.052 dL/g) than PEG (1.308 dL/g), which again suggests that LPG has a highly compact structure in solution. The intrinsic viscosity of polyglycerol increases with increasing molecular weight (similar to proteins) and is significantly lower than other linear polymers.

The transplant preservation solutions of the present invention may have a pH between about 2.0 and about 9.0 or between about 6.5 and about 7.5.

The transplant preservation solutions of the present invention may be in aqueous solution, wherein the polylglycerol comprises about 0.01% by weight to about 50% by weight of the solution or between about 1.25% by weight to about 20% by weight of the solution. For example, 1.25 wt. % of 0.5 kDa HPG to 20 wt. % of 0.5 kDa HPG.

The transplant preservation solutions of the present invention may have an osmolarity between about 150 milliosmols per litre and about 1500 milliosmols per litre. For organ transplant applications, the osmolarity may be between about 290 milliosmols per litre and about 450 milliosmols per litre. For ex vivo applications, high osmolarity may be used; for example, about 1500 milliosmols per litre may be achieved using about 40 wt. % to about 50 wt. % 0.5 kDa HPG solutions. With lower molecular weight HPGs, this osmolarity may be achieved with about 30 wt. % to about 40 wt. % HPG solutions.

The transplant preservation solutions of the present invention may have a polydispersity between about 1.0 and 15.

In some embodiments, the transplant preservation solutions of the present invention may comprise at least two polyglycerols wherein the molecular weight of each of the at least two polyglycerols is different. The molecular weights of each of the at least two polyglycerols may vary by as little as 74 Da, corresponding to the approximate weight of one repeat unit. The molecular weights may also vary by amounts such as about 0.5 kDa, about 1 kDa or about 2 kDa.

In some embodiments, the transplant preservation solutions of the present invention may comprise polyglycerols of a single molecular weight. In some of these embodiments, the transplant preservation solution comprises only a single polyglycerol and in other embodiments the transplant preservation solution comprises at least two polyglycerols having the same molecular weight but different chemical structures.

The polyglycerols as described herein may be derivatized. Derivatives of polyglycerol may include polymers which contain hydrophobic groups, hydrophilic groups or both. Such regions may be provided by derivatizing the hydroxyl groups of the polymer. A functional derivative may be bound to about 1% to about 100% of hydroxyl groups on the polyglycerol, or to about 1% to about 40% of hydroxyl groups on the polyglycerol. Inclusion of such groups in the polyglycerol may result in the number of hydroxyl groups no longer being equal to the number of repeat units in the polyglycerol. Methodologies for adding such groups to a polyglycerol are known to a person of ordinary skill in the art (Beaudette, P., Rossi, N. A. A., Huesgen, P. F., Yu, X., Shenoi, R. A., Doucet, A., Overall, C. M., Kizhakkedathu, J. N., 2011. Development of soluble ester-linked aldehyde polymers for proteomics. Anal Chem 83, 6500-6510; Calderon, M., Quadir, M. A., Sharma, S. K., Haag, R., 2010. Dendritic polyglycerols for biomedical applications. Adv Mater 22, 190-218; Dernedde, J., Rausch, A., Weinhart, M., Enders, S., Tauber, R., Licha, K., Schirner, M., Zugel, U., von Bonin, A., Haag, R., 2010. Dendritic polyglycerol sulfates as multivalent inhibitors of inflammation. Proc Natl Acad Sci USA 107, 19679-19684; Kainthan, R. K., Gnanamani, M., Ganguli, M., Ghosh, T., Brooks, D. E., Maiti, S., Kizhakkedathu, J. N., 2006a. Blood compatibility of novel water soluble hyperbranched polyglycerol-based multivalent cationic polymers and their interaction with DNA. Biomaterials 27, 5377-5390; Kainthan, R. K., Janzen, J., Kizhakkedathu, J. N., Devine, D. V., Brooks, D. E., 2008. Hydrophobically derivatized hyperbranched polyglycerol as a human serum albumin substitute. Biomaterials 29, 1693-1704; Kizhakkedathu, J. N., Creagh, A. L., Shenoi, R. A., Rossi, N. A., Brooks, D. E., Chan, T., Lam, J., Dandepally, S. R., Haynes, C. A., 2010. High molecular weight polyglycerol-based multivalent mannose conjugates. Biomacromolecules 11, 2567-2575; Turk, H., Haag, R., Alban, S., 2004.

Dendritic polyglycerol sulfates as new heparin analogues and potent inhibitors of the complement system. Bioconjug Chem 15, 162-167; and Wilms, D., Stiriba, S. E., Frey, H., 2010. Hyperbranched polyglycerols: from the controlled synthesis of biocompatible polyether polyols to multipurpose applications. Acc Chem Res 43, 129-141). Examples of hydrophobic groups and hydrophilic groups include a carboxylic acid, an amine, a substituted amine, an amino acid, a phosphate, a sulfate, an alkyl, an alkyl ether, an aromatic, a zwitterionic group, a carbohydrate, a disulfide or a thiol.

The transplant preservation solution as described herein may further comprise one or more electrolytes, one or more amino acids, one or more diffusion agents, one or more antioxidants, one or more growth factors, one or more buffering agents, one or more anti-cell death agents and/or one or more osmotic agents. The diffusion agent or osmotic agent may comprise sodium, chloride, bicarbonate, a bicarbonate producing agent, sulfate, phosphate, calcium, potassium, magnesium, latobionate, dextrose, fructose, glycerol, sorbitol, manitol, L-carnitine, bovine serum albumin (BSA), maltose, maltotriose, maltopentose, xylitol, adenosine, glutathione, lactobionic acid, potassium hydroxide or mixtures thereof. The buffering agent may comprise maleic acid, phosphoric acid, sulfate, citric acid, malic acid, formic acid, lactic acid, succinic acid, acetic acid, pivalic (trimethylacetic acid), pyridine, piperazine, picolinic acid, L-histidine, 3-(N-morpholino)propanesulfonic acid (MOPS), 4-(2-hydroxyethyl)-1-piperazineethanesulfonic acid (HEPES), tricine, glycyglycine, bicine, boric acid, glycine, or mixtures thereof.

The transplant preservation solution as described herein may be used in the process of organ transplantation. The organ transplantation may be conducted for a mammal.

Cold ischemic injury during hypothermic preservation of a donor organ, together with additional injury from rewarming or reperfusion, largely contributes to poor organ function in the immediate post-transplantation as well as subsequent rejection episodes (Garlicki, M., 2003. May preservation solution affect the incidence of graft vasculopathy in transplanted heart? Ann Transplant 8, 19-24; Hilmi, I., Horton, C. N., Planinsic, R. M., Sakai, T., Nicolau-Raducu, R., Damian, D., Gligor, S., Marcos, A., 2008. The impact of postreperfusion syndrome on short-term patient and liver allograft outcome in patients undergoing orthotopic liver transplantation. Liver Transpl 14, 504-508; and Lauzurica, R., Pastor, M. C., Bayes, B., Hernandez, J. M., Bonet, J., Dolade, M., Navarro, M., Romero, R., 2008. Pretransplant inflammation: a risk factor for delayed graft function? J Nephrol 21, 221-228). Transplant preservation solution may enhance the protection of donor organs from cold ischemic injury, and of human endothelial cells from cold-induced cell death.

Donor organs stored and transported at hypothermic temperatures (0-5° C.), results in cessation of aerobic metabolism and avoids warm ischemic injury during organ procurement and transport. Transplant preservation solution may be an effective method in clinical practice to prolong the storage period, and the use of transplant preservation solutions as a hypothermic preservation solution prevents the cells from swelling during cold ischemic storage.

Keeping endothelial cell viability or endothelial monolayer integrity is helpful for successfully limiting vascular permeability of solid organs after transplantation. When the blood in a donor organ is replaced by a cold preservation solution for its cold preservation prior to transplantation, vascular endothelium is often first to interact with the cold environment. Loss of endothelial integrity often represents a primary event in cold preservation-related graft injury in various organ transplants. Cold injury may impair the barrier function of the endothelium, leading to parenchymal edema and hemorrhage following reperfusion and early graft dysfunction. Transplant preservation solutions of the present invention may increase the protection of cultured endothelial cells from necrosis, and may reduce grafts injury during cold preservation. Improved functional recovery, reduced perivascular inflammation, reduced cellular infiltration, and prolonged graft survival after transplantation may be observed using transplant preservation solutions of the present invention.

The cell membrane may be a site of cold-induced injury. When cells are transferred to a cold temperature, cell membranes may be destabilized by, for example, a change of membrane structure. Examples include, modifications of specific lipid-protein interaction, phospholipid asymmetry and lipid composition. A membrane transition from the liquid-crystalline phase to the gel phase can result in cell death. Cold transplant preservation solution can prevent such a transition as well as other cold-induced injuries.

The transplant preservation solution of the present invention may be included in a kit for formulating a transplant preservation solution. The kit may comprise a lyophilized polyglycerol as described herein and instructions for using the lyophilized polyglycerol for formulating the transplant preservation solution. The kit may comprise other components of the transplant preservation solution, including electrolytes, amino acids, one or more other diffusion agents and/or one or more other osmotic agents.

The transplant preservation solution as described herein may be included in a composition. The composition may comprise HPG as described herein and at least one physiologically acceptable salt, buffer, diluent and/or excipient, for use as a transplant preservation solution. The composition may be in aqueous solution or a lyophilized product.

Various alternative embodiments and examples are described herein. These embodiments and examples are illustrative and do not limit the scope of the invention.

EXAMPLES

C57BL/6j (B6) and BALB/c mice (males, 8-10 weeks old) were purchased from the Jackson Laboratory (Bar Harbor, Me., USA). All the procedures related to animal use in this study were performed and monitored in accordance with the Canadian Council on Animal Care guideline under the protocols approved by the Animal Use Subcommittee at the University of British Columbia. Primary human umbilical vein endothelial cells (HUVECs) were purchased from Lonza Walkersville Inc (Walkersville, Md., USA), and were immortalized with origin-deficient SV40 DNA for experiments in our laboratory. The endothelial cell cultures were maintained and grown in Medium 199 supplemented with 10% bovine calf serum, endothelial cell growth supplement, 50 μg/mL heparin, and antibiotics (penicillin and streptomycin)(Sigma-Aldrich, St. Louis, Mo., USA) at 37° C. under 5% $CO_2$.

Data were presented as mean±standard error of the mean (SEM). The statistical significance of the difference between two groups was determined by t-test. One-way analysis of variance (ANOVA) or two-way with Tukey's multiple comparison test was used as appropriate for comparisons among multiple groups. Values of p 0.05 were considered statistically significant.

Example 1: Reduced Organ Damage in Hypothermic Storage of Isolated Hearts with HPG Solution To demonstrate the beneficial effect of HPG solution in comparison to UW solution on the prevention of cold ischemia injury during cold storage of donor organs, the tissue damage of isolated mouse hearts preserved with HPG solution versus UW solution (0.2 mL/organ at 4° C.) was determined by LDH release from donor tissues at different time points. As shown in FIG. 1A, the levels of LDH in the supernatant, released from damaged tissue or dead cells of the organ, were increased with increasing the hypothermic storage time for both UW and HPG solution, but the amount of LDH was significantly lower with HPG solution compared to UW solution. The LDH level for HPG group was increased from 0.75±0.43 at 2 h to 1.71±0.55 at 24 h in comparison to 1.15±0.22 at 2 h to 2.46±0.24 at 24 h in UW group ($P<0.0001$, two-way ANOVA, n=4-7). Enhanced protection of organs was indicated by the lower levels of LDH release from the hearts in HPG group compared to UW group which was further confirmed by ethidium bromide (EB) staining (FIG. 1B). EB is a cell membrane impermeable fluorescent dye that stains nucleic acids, and has been used for dead cell staining. As shown in FIG. 1B, the intensity of EB staining of the hearts after 24 h with HPG solution was weaker than that stored in UW solution. These data suggest that hypothermic storage of isolated mouse hearts with HPG solution results in less organ damage as compared to UW solution.

Figure 2:
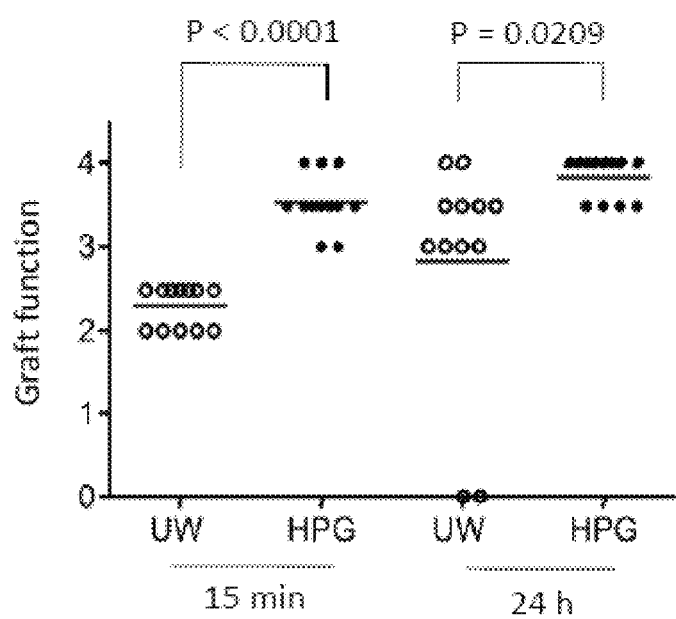
FIG. 2: Cold preservation of donor hearts in HPG solution enhances functional recovery after transplantation. Donor hearts were harvested from naïve B6 mice, and were stored in HPG or UW solution (0.5 mL/organ) at 4° C. for 24 h. After transplantation to syngeneic B6 recipient mice, the graft function that was determined by the clinical score of graft contraction/beating was examined at both 15 min and 24 h post-transplantation. Score 4: normal contraction (equal to <30 minutes of cold preservation in UW solution). At 15 min, p<0.0001 (t-test, HPG vs. UW). At 24 h, p=0.0209 (t-test, HPG vs. UW).

Example 2: Improvement of Functional Recovery of Heart Transplants with Less Tissue Damage in Syngeneic Recipients after Hypothermic Storage with HPG Solution To further examine if the enhanced organ protection of donor organs after cold storage in HPG solution could be translated to their functional recovery after transplantation, the hearts from B6 mice after 24 h of cold storage at 4° C. with HPG solution (5 mL/organ) were heterotopically transplanted to syngeneic B6 mice. A similar experiment was performed with hearts stored in UW solution. The function of grafts was examined at both 15 min and 24 h after surgery. As shown in FIG. 2, the clinical score of graft function of heart grafts pretreated with HPG solution was significantly higher than those stored in UW solution at both two time points. The mean score 3.542 in HPG solution group compared to 2.292 in UW solution group at 15 min (P<0.0001), or 3.833 in HPG solution group compared to 2.833 in UW solution group (P=0.0209) at 24 h. In the case of UW solution group, 2 out of 12 grafts lost their function at 24 h time point. These data suggest that donor hearts after a prolonged cold preservation with HPG solution have a better functional recovery than those in UW solution after transplantation.

Figure 3:
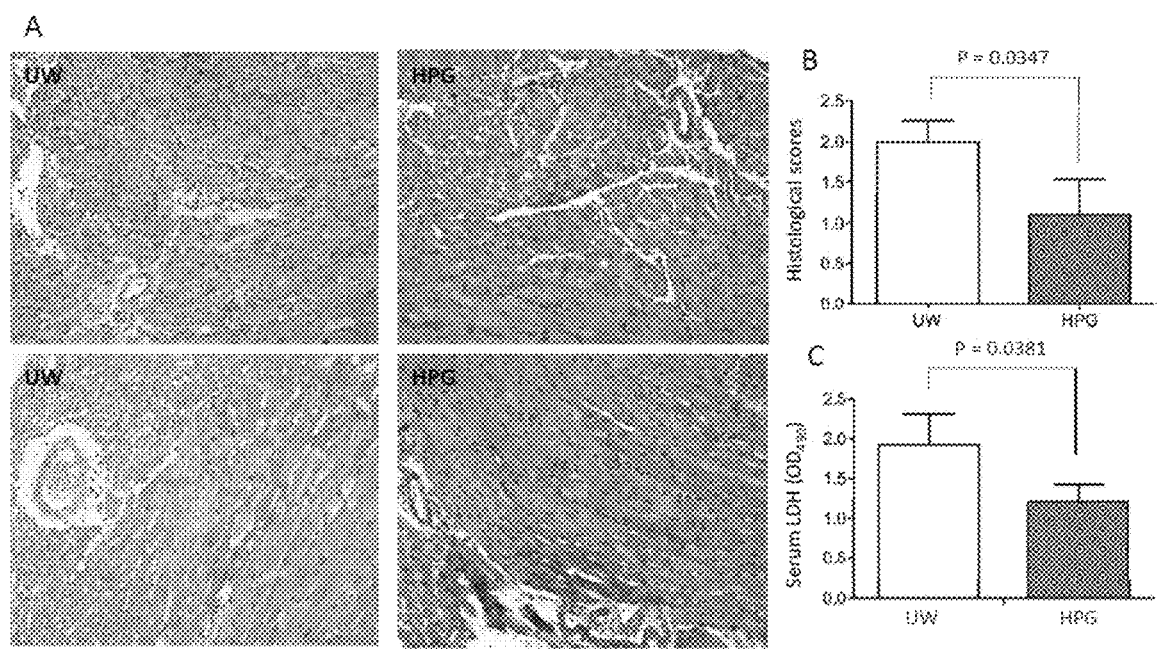
FIG. 3: Cold preservation with HPG solution reduces cardiac inflammation and cell death in heart transplants. Donor hearts were treated with prolonged cold preservation in HPG solution versus UW solution and transplanted as described in FIG. 2. The grafts were harvested at 24 h after transplantation, and were formalin-fixed and paraffin-embedded. (A) The graft injury was examined in H&E stained sections. Data are presented as a typical image of light microscopy, showing perivascular inflammation and cardiaomyocyte necrosis. (B) Histological scores of the graft injury in HPG versus UW solution group. Data are presented as mean±SEM in each group (p=0.0347, t-Test, HPG vs. UW, n=9-10). (C) The graft injury was determined by the LDH release from heart transplants to the serum. Sera were harvested from recipients at 24 h after transplantation, and serum levels of LDH as a biochemical marker of cardiac graft injury were quantitatively measured using cytotoxicity detection kit. Data are presented as mean±SEM of ten recipients in each group (p=0.0381, t-test, HPG vs. UW).

To further understand the reason why transplants preserved in HPG solution had better functional recovery, the tissue injury and neutrophil infiltration in heart grafts were examined at 24 h after transplantation. Sections of heart grafts stained with H&E stain showed that hearts stored in HPG solution exhibited less perivascular inflammation and cardiaomyocyte necrosis compared to the grafts stored in UW solution (FIG. 3A). The result was confirmed by the semiquantitative scoring (FIG. 3B), indicating a significantly lower score (1.111±0.423) in HPG solution group as compared to 2.0±0.258 in UW solution group (P=0.0347). The lower serum levels of LDH in recipient mice receiving HPG solution-preserved grafts further confirmed less tissue damage in histological analysis. FIG. 3C showed the LDH levels in serum, represented by the absorbance value in the measurement, in recipients in the HPG group were 1.21±0.76, significantly lower than in the UW group 1.97±1.34 (p=0.0381).

Figure 4:
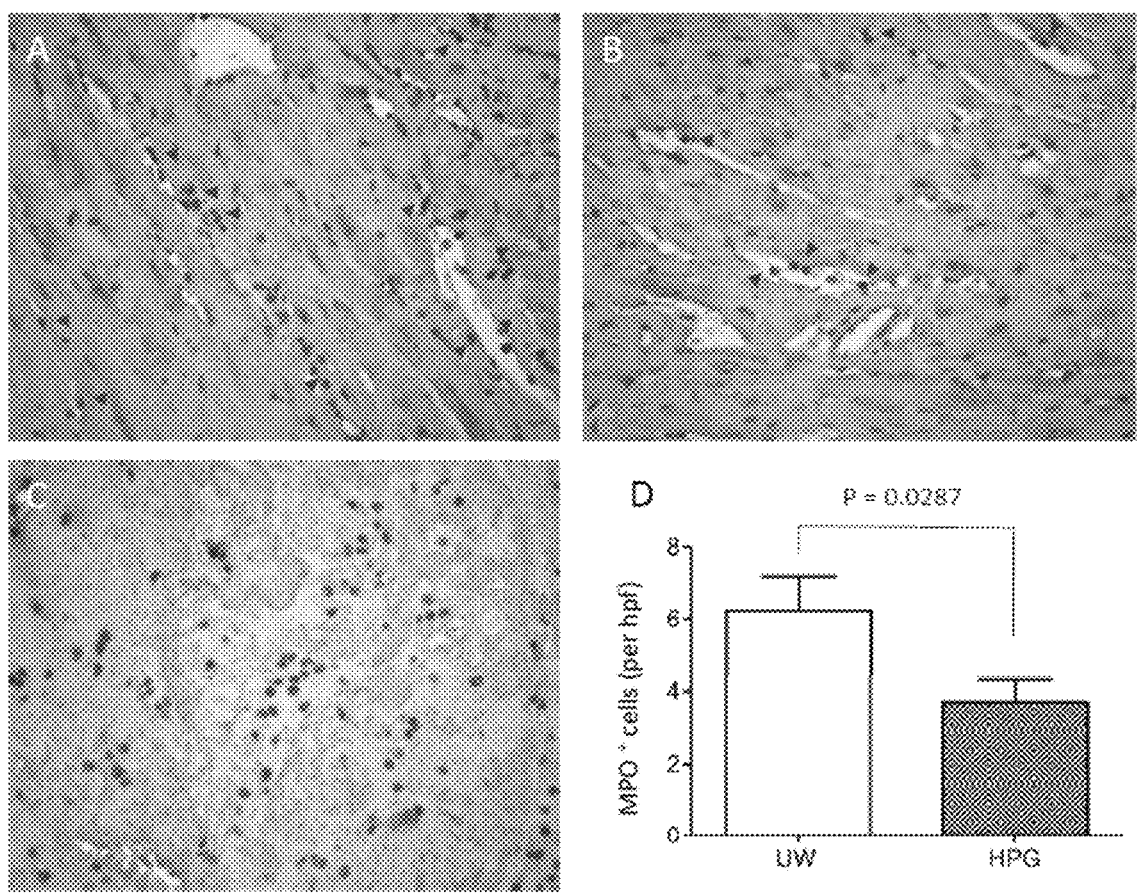
FIG. 4: Cold preservation with HPG solution reduces myeloperoxidase (MPO)-positive infiltration in heart transplants. MPO-positive cells in the sections of cardiac isografts were detected by immunohistochemical stain with anti-MPO antibody. The data are presented as a typical microscopic view in each group: (A) UW group; (B) HPG group; and (C) Positive control, blood clot. Red arrows point MPO-positive cells in the sections. (D) The number of MPO-positive infiltrates counted using a microscope under 400× magnification (high-powered field, or hpf). The view was not overlapped and was randomly selected. At least 25 views from two separate sections were counted and averaged for each graft. Data are presented as mean±SEM of six grafts in each group (p=0.0287, t-Test, HPG vs. UW).

Neutrophils are one of the first-responding inflammatory cells recruited to the site of injury within minutes following trauma, and are the hallmark of acute muscle injury (Tidball J G, 1995). MPO-expressing infiltrates (activated neutrophils) in the cardiac sections were determined using immunohistochemical stain with anti-MPO antibody, and counted with a semiquantitative method. As shown in FIG. 4, immunohistochemical stain of $MPO^+$ infiltrates showed that graft sections in HPG solution group had fewer infiltrating $MPO^+$ cells (3.712±0.615 cells/hpf) than that in UW solution group (6.237±0.921 cells/hpf) (p=0.0287, n=6). Taken together, all these data suggest that cold preservation of donor hearts with HPG solution could improve the recovery of graft function after transplantation, which is associated with less graft injury.

Figure 5:
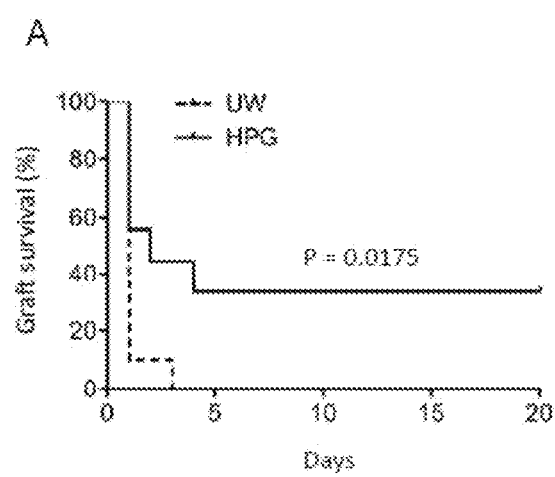
FIG. 5: Cold preservation with HPG solution prolongs survival of cardiac allografts. Donor hearts from naïve B6 mice were stored in HPG or UW solution (0.5 mL/organ) at 4° C. for 24 h, and transplanted into allogeneic BALB/c mice that were treated with CsA daily. Graft survival was assessed by daily transabdominal palpation, and cessation of the graft beat was considered as graft failure. (A) Graft survival in HPG versus UW group (p=0.0175, log-rank test, n=9-10). (B, C) Typical microscopic views of H&E-stained sections of functioning grafts on day 20 post-transplantation.
Figure 5:
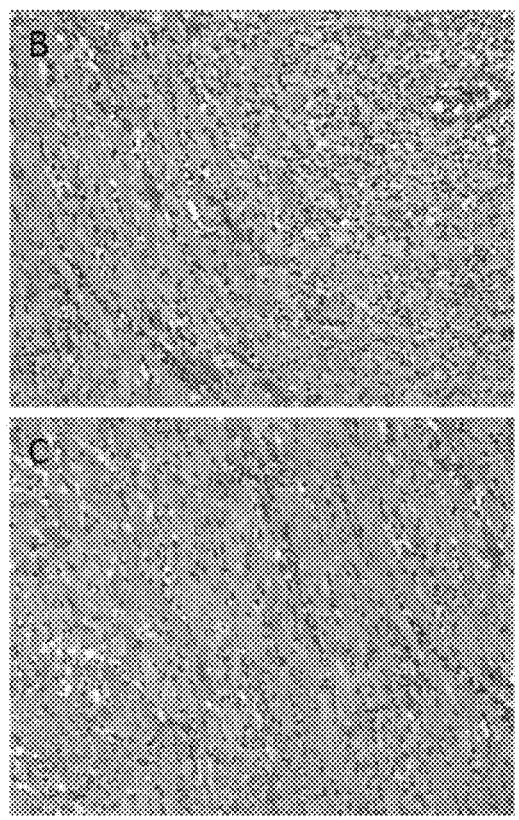

Example 3: Prolonged Survival of Heart Transplants after Hypothermic Storage with HPG Solution In clinical transplantation, donor organs are mostly transplanted into allogeneic recipients, and these allografts survive under immunosuppressive therapy. To test if HPG solution was superior to UW solution in this setting, donor hearts from B6 mice were preserved both with HPG solution and UW solution (5 mL/organ) at 4° C. for 24 h. Stored hearts were heterotopically transplanted to allogeneic BALB/c mice that were receiving daily CsA treatment immediately after surgery. As shown in FIG. 5, allografts preserved with HPG solution survived longer than those stored in UW solution. Only one transplant with UW solution group was survived 3 days, the rest of them failed within 24 h. In comparison, within HPG groups three of the grafts survived with function in CsA-treated recipients until the end of experiment—for 20 days (P=0.0175, Log-rank test) and four out of nine transplants in rejected within 24 h. These data suggest that cold preservation of donor hearts with HPG solution prolongs graft survival in allogeneic recipients.

Figure 6:
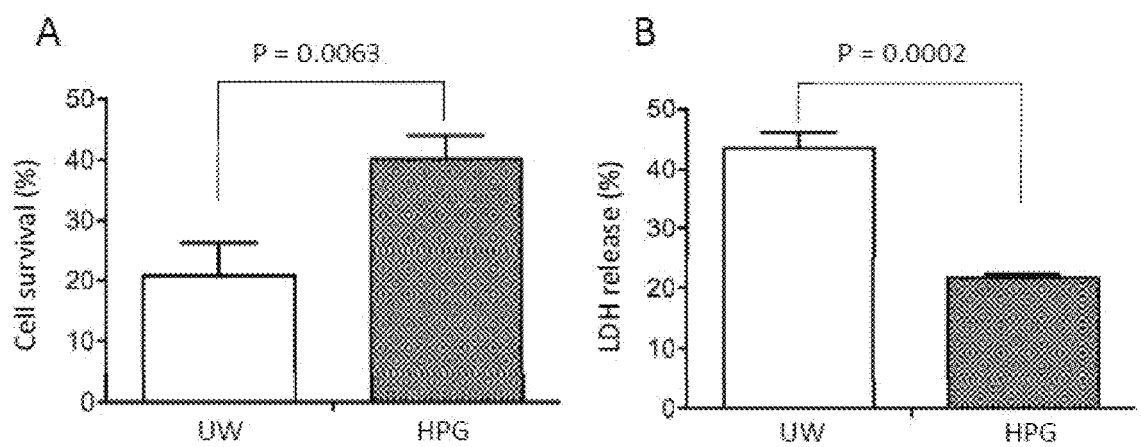
FIG. 6: Cold preservation with HPG solution protects HUVECs from cell lysis at cold temperature. A monolayer of HUVECs in 24-well plates was incubated with HPG versus UW solution at 4° C. for 24 h: (A) Cell survival was determined by trypan blue exclusion assay. Data are presented as mean±SEM of four separate experiments in each group (p=0.0063, t-test, HPG vs. UW). (B) Cell death in the same cultures was confirmed by the measurement of LDH release. LDH in the preservation solution as a marker of cell lysis was measured and was calculated as a percentage of total LDH in a corresponding positive control (UW solution containing 2% Triton-100). Data are presented as mean±SEM of four separate experiments in each group (p=0.0002, t-test, HPG vs. UW).

Example 4: Enhanced Cell Survival in Cultured Human Endothelial Cells by Exposure to HPG Solution at Hypothermic Conditions To further test the advantage of HPG solution over UW solution in hypothermic preservation of donor organs, the impact of these solutions on survival of cultured HUVECs at 4° C. was compared. As shown in FIG. 6, there were more survived cells in cultured HUVECs exposed to HPG solution compared to UW solution, evidenced by significantly more cell survival in HUVECs treated with HPG solution (40.19±3.77%) as compared to those (20.75±2.87%) with UW solution (P=0.0063) (FIG. 7A). The beneficial effect of HPG solution on cell survival was further confirmed by the lower levels of LDH release in HPG solution (21.76±0.29%) compared to those (43.46±2.6%) in UW solution (P=0.0002). The LDH release from HUVEC cultures under the normal culture conditions after 24-h incubation was approximately 21%, suggesting that HPG solution might completely protect cultured human endothelial cells from cell lysis at cold temperature in a period of 24 h.

Figure 7:
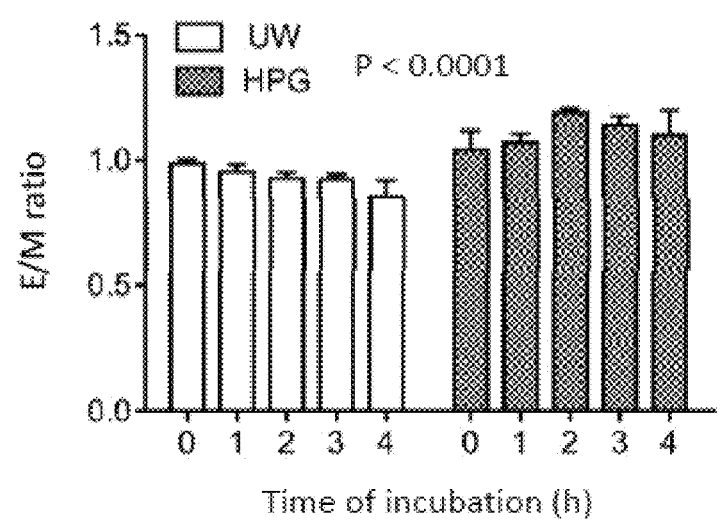
FIG. 7: Cold preservation with HPG solution enhances cell membrane fluidity of HUVECs at cold temperature. The cell membrane fluidity of HUVECs in HPG versus UW solution at 4° C. was monitored with a pyrene eximer for a period of 4 h. The ratio of eximer-to-monomer (E/M) was calculated as an indictor for the membrane fluidity at the various time points. Data are presented as mean±SEM of five separate experiments (p<0.0001, two-way ANOVA, HPG vs. UW).

Example 5: Maintenance of Cell Membrane Fluidity and Intracellular ATP in Hypothermic Preservation with HPG Solution To investigate the reason behind the advantage of HPG solution over UW solution in the hypothermic protection of cultured HUVECs from cell death, their influence on membrane fluidity and intracellular ATP were examined. The cell membrane fluidity was determined by the pyrene eximer formation using a pyrene eximer-forming probe, pyrenedecanoic acid. As shown in FIG. 7, there was a decreasing trend in E/M ratio from 0.99±0.02 at 0 h to 0.85±0.07 at 4 h (P=0.1887, one-way ANOVA, n=3) in HUVECs after cold exposure in UW solution. However, the E/M ratio in these cells with HPG solution remained unchanged in the period of study (4 h), indicated by 1.04±0.07 at 0 h to 1.10±0.1 at 4 h (P=0.4647, one-way ANOVA, n=3). Statistical comparison of the E/M ratio between these groups suggested that the E/M ratio was significantly higher in HUVECs with HPG solution than those with UW solution (P<0.0001, two-way ANOVA). These data suggest that HPG solution may be able to maintain the membrane fluidity in cultured endothelial cells even when exposed to cold temperature, while the membrane fluidity in the cells with UW solution decreased during the cold preservation.

To confirm this observation, both extracellular and intracellular ATP levels in these cells were measured after 4 h of hypothermic preservation with UW and HPG solutions. As listed in Table 1, the extracellular ATP, released from HUVECs after exposure to cold UW solution or HPG solution, was not significantly different (137.14±20.11 pmol vs. 130.04±18.19 pmol, P=0.5740), while the intracellular ATP (50.67±4.03 pmol) of HUVECs with HPG solution was significantly higher than that (43.0±4.4 pmol) of those preserved with UW solution (P=0.0208), which was further supported by the fact that the ratio of extracellular to intracellular ATP in HPG solution group was significantly lower than that in UW solution group (2.55±0.17 vs. 3.18±0.31, P=0.0039). Taken together, the enhanced cell survival in human endothelial cells at cold temperature with HPG solution in comparison to UW solution is positively correlated with its capacity of maintaining membrane fluidity and ATP biosynthesis.

Example 6: Preparation of HPG Solution

HPG polymer (0.5, 1, 3.5 kDa) was synthesized by anionic ring opening multi-branching polymerization of glycidol as described previously (Sunder, A., Hanselmann, R., Frey, H., Mulhaupt, R., 1999. Controlled synthesis of hyperbranched polyglycerols by ring-opening multibranching polymerization. Macromolecules 32, 4240-4246). The molecular characteristics of the polymer were determined by gel permeation chromatography and proton nuclear magnetic resonance spectroscopy. HPG was purified by dialysis against MilliQ filtered water and lyophilized. HPG-based preservation solutions were prepared by dissolving HPG (3%, w/v) in a solution containing: 100 mM lactobionic acid, 100 mM potassium hydroxide (KOH), 25 mM potassium dihydrogen phosphate ($KH_2PO_4$), 5 mM magnesium sulfate ($MgSO_4$), 5 mM adenosine, 3 mM glutathione, and 1 mM allopurinol, the same composition as in Viaspan™ UW solution (UW solution, DuPont Canada, Mississauga, ON, Canada) omitting 30 mM raffinose and 5% HES. The pH of HPG preservation solution was adjusted to 7.4 using NaOH/HCl at 22° C., and its osmolality (~320 mOsm/kg) was determined using Advanced® Model 3320 Micro-Osmometer (Advanced Instruments, Inc., Norwood, Mass., USA) in the Vancouver Coastal Health Regional Laboratory Medicine (Vancouver, BC, Canada).

Example 7: Donor Preservation and Heterotopic Cardiac Transplantation

Donor hearts were harvested from B6 donor mice after perfusion with 10 units/mL of heparin, and stored with ligated pulmonary veins in HPG solution versus UW solution at 4° C. After 24 h of cold preservation, the donor hearts were heterotopically transplanted into either syngeneic B6 mice (isotransplantation) or allogeneic BALB/c mice (allotransplantation) as described previously (Li, S., Guan, Q., Chen, Z., Gleave, M. E., Nguan, C. Y., Du, C., 2011. Reduction of cold ischemia-reperfusion injury by graft-expressing clusterin in heart transplantation. J Heart Lung Transplant 30, 819-826). The graft function was scored by its contraction or beating at both 15 min and 24 h after graft transplantation according to a semiquantitation method as described previously (Kuznetsov, A. V., Schneeberger, S., Seiler, R., Brandacher, G., Mark, W., Steurer, W., Saks, V., Usson, Y., Margreiter, R., Gnaiger, E., 2004. Mitochondrial defects and heterogeneous cytochrome c release after cardiac cold ischemia and reperfusion. Am J Physiol Heart Circ Physiol 286, H1633-1641; and Li, S., Guan, Q., Chen, Z., Gleave, M. E., Nguan, C. Y., Du, C., 2011. Reduction of cold ischemia-reperfusion injury by graft-expressing clusterin in heart transplantation. J Heart Lung Transplant 30, 819-826). In allotransplantation, after surgery the recipient mice received cyclosporine (CsA) therapy (15 mg/kg/day, Novartis, Basel, Switzerland) immediately until the end of experiment or for 20 days. Graft survival was assessed by daily transabdominal palpation in a blinded fashion. Cessation of heartbeat indicated the failure of heart transplant, which was subsequently confirmed by histological examination.

Example 8: Measurement of Lactate Dehydrogenase (LDH)

Cell death with cell membrane disruption and/or cardiac injury was determined by LDH release, that was quantitated by LDH assay using cytotoxicity detection kit (Roche Applied Science, Laval, QC) following manufacturers' protocols. In cultured cells, LDH release in the preservation solution was presented as a percentage of positive control (cells incubating with 2% Triton X-100), or in mice, LDH release in the sera as an absorbance unit ($OD_{490}$).

Example 9: Semiquantitation of Cell Viability by Trypan Blue Exclusion Assay Cell viability was assessed by negatively staining with trypan blue, a cell membrane impermeable dye. In brief, a confluent monolayer of HUVECs ($0.2 \times 10^6$ cells/well) in 24-well plates was grown overnight, followed by incubation with 0.5 mL of HPG solution or UW solution at 4° C. After hypothermic preservation for 24 h, cells were detached with trypin-EDTA solution (Sigma-Aldrich Canada), and the viable, survived cells, stained negatively with trypan blue, were automatically counted by using TC10™ automated cell counter (Bio-Rad Laboratories Canada, Mississauga, ON, Canada). The percentage of survived cells was calculated as follows: $\% = (T_x/T_0) \times 100$, where $T_x$ represented the total number of viable cells at indicated time point, and $T_0$ indicated the total number of viable cells in untreated cell monolayer (0 h time point). The number of viable cells in each sample was presented by the average of at least three determinants.

Example 10: Evaluation of Cell Membrane Fluidity

The cell membrane fluidity of cultured HUVECs was measured using a membrane fluidity kit following the manufacturer's protocol (Marker Gene Technologies, Eugene, Oreg., USA).

HUVECs ($1\times10^6$ cells/ml) in culture medium were labeled with lipid analog probe pyrenedecanoic acid by incubation at 25° C. for 20 minutes. After two washes with PBS, the cells were incubated in HPG solution or UW solution at 4° C. The emission of monomer (M) at 390 nm or eximer (E) at 480 nm of the probe in the cell membrane was monitored using a fluorescence spectrometer at an excitation of 340 nm at 4° C. for a period of 6 h. The E/M ratio was calculated as an indicator of membrane fluidity Example 11: Immunohistochemical Analysis Myeloperoxidase (MPO), a biomarker of infiltrating neutrophils, in the sections of cardiac tissues was localized by a standard immunohistochemical method, and MPO$^+$ infiltrates was semiquantitated as described previously (Guan, Q., Li, S., Yip, G., Gleave, M. E., Nguan, C. Y., Du, C., 2012. Decrease in donor heart injury by recombinant clusterin protein in cold preservation with University of Wisconsin solution. Surgery 151, 364-371; and Li, S., Guan, Q., Chen, Z., Gleave, M. E., Nguan, C. Y., Du, C., 2011. Reduction of cold ischemia-reperfusion injury by graft-expressing clusterin in heart transplantation. J Heart Lung Transplant 30, 819-826).

Example 12: Measurement of Adenosine Triphosphate

The levels of adenosine triphosphate (ATP) in the solutions or cellular extracts were measured by using an ATP determination kit following the manufacturer's protocol (Invitrogen—Life Technologies Inc., Burlington, ON, Canada). In brief, HUVECs ($1\times10^6$ cells/well) were grown in culture medium in 6-well plates overnight, followed by exposure to HPG solution versus UW solution (0.5 mL/well) at 4° C. for 4 h. After collection of the solution/supernatant, the intracellular ATP was extracted by the incubation of the cell with 0.35 mL/well of Somatic Cell ATP Releasing Agent (Sigma-Aldrich Canada). Both extracellular ATP in the supernatant and intracellular ATP levels in each experiment were calculated based on the ATP standards determined in the same assay.

Example 13: Histological Analysis of Graft Injury

After phosphate-buffered saline (PBS) perfusion, tissue samples were removed at necropsy and fixed in 10% buffered formaldehyde. Specimens were then embedded in paraffin, and sectioned for the hematoxylin and eosin (H&E) staining. Graft injury was determined in H&E-stained sections by histological analysis, and was pathologically scored in a blinded fashion based on the severity of cardiac tissue damage under the microscopic view as: 0: normal cardiac tissue; 1: mild damage, indicated by perivascular injury; 2: severe damage, indicated by the presence of both perivascular injury and mild cardiac hemorrhaging; or 3: severe hemorrhaging and cardiac dilation.

Figure 8:
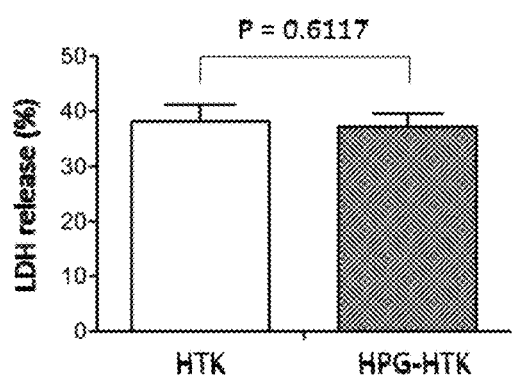
FIG. 8: Effects of the molecular weight of HPG on cold preservation of mouse hearts are shown in four graphs showing the percent LDH release of various different solutions over time and at different temperatures.
Figure 8:
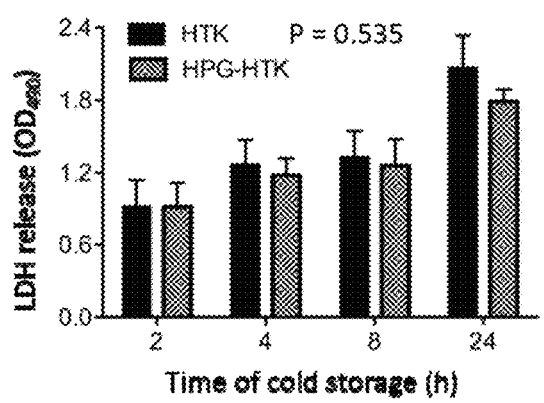
Figure 8:
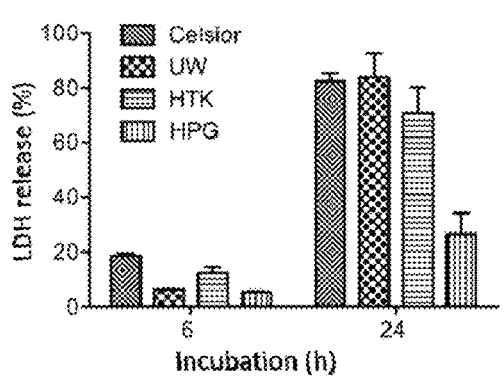
Figure 8:
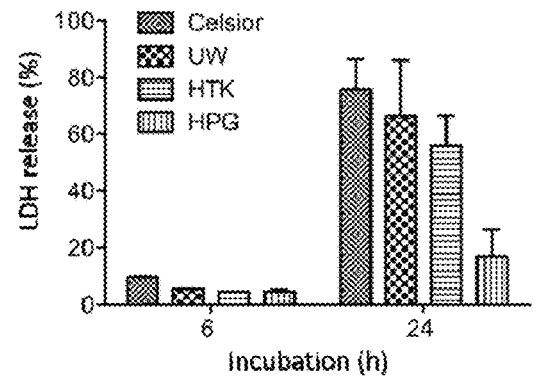

Example 14: The Effect of Molecular Weight of HPG on Cold Preservation of Mouse Hearts An experiment to test the effects of the molecular weight of HPG on cold preservation of mouse hearts was also conducted using a protocol similar to Example 1. The results of this experiment are set out in the table below and further in FIG. 8.

| The effect of molecular weight of HPG on cold preservation of mouse hearts | | | |
|---|---|---|---|
| Group* | 6 h** | 24 h | P value*** |
| UW solution | 1.991 ± 0.104 | 2.325 ± 0.169 | |
| 0.5 kDa HPG | 1.046 ± 0.353 | 1.723 ± 0.304 | 0.0007 |
| 1 kDa HPG | 0.739 ± 0.165 | 1.593 ± 0.148 | <0.0001 |
| 3.5 kDa HPG | 0.987 ± 0.039 | 1.713 ± 0.346 | 0.0001 |
| 8.7 kDa HPG | 1.129 ± 0.479 | 1.780 ± 0.699 | 0.0064 |
| 10 kDa HPG | 1.524 ± 0.470 | 2.048 ± 0.423 | 0.0881 |
| 25 kDa HPG | 1.705 ± 0.754 | 2.182 ± 0.678 | 0.4919 |
| 52 kDa HPG | 1.661 ± 0.254 | 2.152 ± 0.216 | 0.0550 |
| 119 kDa HPG | 1.833 ± 0.386 | 2.413 ± 0.175 | 0.8003 |

*All the HPG solutions contained 3% (w/v) of HPG.
**Mouse heart damage after preservation at 4° C. for 6 or 24 h was determined by LDH release, and was presented by the absorbance at LDH measurement.
***The difference between UW solution and each HPG solution was statistically analyzed by two-way ANOVA (n = 3).
P ≤ 0.05 was considered significant.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings. Citation of references herein is not an admission that such references are prior art to the present invention nor does it constitute any admission as to the contents or date of these documents.

What is claimed is:

1. A method of reducing damaging effects of cold ischemia and warm reperfusion in organ, tissue, or cell function during organ procurement and transplantation, the method comprising:

administering a transplant preservation solution to a donor organ, the transplant preservation solution comprising at least one hyperbranched or dendritic polyglycerol in a UW-type solution, wherein the UW-type solution comprises lactobionic acid, potassium hydroxide, potassium dihydrogen phosphate, magnesium sulfate, adenosine, glutathione and allopurinol, wherein the at least one hyperbranched or dendritic polyglycerol has a molecular weight between 0.48 kDa and 3.00 kDa, and wherein the UW-type solution does not comprise raffinose or hydroxyethyl starch.

2. The method of claim 1, wherein the transplant preservation solution has a pH between about 2.0 and about 9.0.

3. The method of claim 1, wherein the transplant preservation solution is an aqueous solution, and wherein the hyperbranched or dendritic polyglycerol comprises about 0.01% to about 50% by weight of the transplant preservation solution.

4. The method of claim 1, wherein the transplant preservation solution has an osmolarity between about 150 milliosmols per litre and about 1500 milliosmols per litre.

5. The method of claim 1, wherein the hyperbranched or dendritic polyglycerol has a polydispersity of about 1.0 to about 15.

6. The method of claim 1, wherein the transplant preservation solution comprises at least two hyperbranched or dendritic polyglycerols, and wherein the molecular weight of each of the at least two hyperbranched or dendritic polyglycerols is different.

7. The method of claim 1, wherein the branched or dendritic polyglycerol further comprises one or more hydrophobic groups, hydrophilic groups, or both.

8. The method of claim 7, wherein the one or more hydrophobic groups, hydrophilic groups, or both are joined to about 1% to about 100% of hydroxyl groups on the hyperbranched or dendritic polyglycerol.

9. The method of claim 7, wherein the one or more hydrophobic groups, hydrophilic groups, or both are joined to about 1% to about 40% of hydroxyl groups on the hyperbranched or dendritic polyglycerol.

10. The method of claim 1, wherein the one or more hydrophobic groups, hydrophilic groups or both comprise one or more of a carboxylic acid, an amine, a substituted amine, a quaternary amine, an amino acid, a phosphate, a sulfate, a sulfonate, a phosphonate, an alkyd, an alkene, an alkyne, an alkyl ether, an aromatic, an aromatic ether, a zwitterionic group, a carbohydrate, a disulfide, a ketal, a substituted ketal, an acetal, a substituted acetal, ester groups, thioesters, a urethane, ester-amides, amide groups, a peptide, a phenol, halogens, or a thiol.

11. The method of claim 1, wherein the transplant preservation solution further comprises at least one component selected from the group consisting of one or more electrolytes, one or more xanthine oxidase inhibitors, one or more antioxidants, one or more nucleosides, one or more amino acids, one or more diffusion agents, one or more osmotic agents, one or more growth factors, one or more buffering agents, and one or more anti-cell death agents.

12. The method of claim 9, wherein the transplant preservation comprises at least one osmotic agent or diffusion agent selected from sodium, chloride, bicarbonate, a bicarbonate producing agent, sulfate, phosphate, calcium, potassium, magnesium, lactobionate, dextrose, fructose, glycerol, sorbitol, manitol, L-carnitine, bovine serum albumin (BSA), maltose, maltotriose, maltopentose, xylitol, adenosine, glutathione, synthetic polymers, and natural polymers.

13. The method of claim 9, wherein the transplant preservation solution comprises at least one buffering agent selected from maleic acid, phosphoric acid, sulfate, citric acid, malic acid, formic acid, lactic acid, succinic acid, acetic acid, pivalic acid, pyridine, piperazine, picolinic acid, L-histidine, 3-(N-morpholino)propanesulfonic acid (MOPS), 4-(2-hydroxyethyl)-1-piperazineethanesulfonic acid (HEPES), tricine, glycyglycine, bicine, boric acid, and glycine.

14. The method of claim 1, wherein the transplant preservation solution is administered to the donor organ for preservation of the donor organ during transportation of the donor organ ex-vivo.

15. The method of claim 12, further comprising procuring the donor organ from a first patient prior to administering the transplant preservation solution to the donor organ.

16. The method of claim 13, further comprising transplanting the donor organ to a second patient.

17. The method of claim 1, wherein the transplant preservation solution is administered to the donor organ at a temperature between about 0° C. and about 25° C.

18. The method of claim 1, wherein the transplant preservation solution is administered to the donor organ at a temperature between about 1° C. and about 10° C.

19. The method of claim 1, wherein the transplant preservation solution is administered to the donor organ at a temperature between about 25° C. and about 40° C.

20. A method of treating a donor organ to reduce the damaging effects of cold ischemia and warm reperfusion on organ function, the method comprising:
procuring a donor organ from a first patient;
administering a transplant preservation solution to the donor organ, the transplant preservation solution comprising at least one hyperbranched or dendritic polyglycerol in a UW-type solution, wherein the UW-type solution comprising lactobionic acid, potassium hydroxide, potassium dihydrogen phosphate, magnesium sulfate, adenosine, glutathione and allopurinol, wherein the at least one hyperbranched or dendritic polyglycerol has a molecular weight between 0.48 kDa and 3.00 kDa, and wherein the UW-type solution does not comprise raffinose or hydroxyethyl starch;
transporting the donor organ ex-vivo while being maintained in the transplant preservation solution; and
transplanting the donor organ.

21. The method of treating a donor organ of claim 20, wherein the step of administering the transplant preservation solution to the donor organ is conducted at least once per day.

22. A method of reducing damaging effects of cold ischemia and warm reperfusion in organ, tissue, or cell function during organ procurement and transplantation, the method comprising:
procuring a donor organ from a first patient;
administering a transplant preservation solution to the donor organ, the transplant preservation solution comprising at least one hyperbranched or dendritic polyglycerol in a UW-type solution, wherein the UW-type solution comprises lactobionic acid, potassium hydroxide, potassium dihydrogen phosphate, magnesium sulfate, adenosine, glutathione and allopurinol, wherein the at least one hyperbranched or dendritic polyglycerol has a molecular weight between 0.48 kDa and 3.00 kDa, and wherein the UW-type solution does not comprise raffinose or hydroxyethyl starch, thereby preparing the donor organ in order to reduce damaging effects of cold ischemia and warm reperfusion in the donor organ during organ procurement, transportation and transplantation;

transporting the donor organ; and transplanting the donor organ to a second patient.

* * * * *